United States Patent [19]
Berge et al.

[11] Patent Number: 5,093,365
[45] Date of Patent: Mar. 3, 1992

[54] NON-β-OXIDIZABLE FATTY ACID ANALOGUES WITH THE EFFECT TO REDUCE THE CONCENTRATION OF CHOLESTEROL AND TRIGLYCERIDES IN BLOOD OF MAMMALS

[75] Inventors: Rolf K. Berge, Bones; Jon Bremer, Oslo, both of Norway

[73] Assignee: Norsk Hydro A.S., Oslo, Norway

[21] Appl. No.: 360,870

[22] Filed: Jun. 2, 1989

[30] Foreign Application Priority Data

Jun. 2, 1988 [GB] United Kingdom ............... 8813012

[51] Int. Cl.$^5$ .................... A01N 37/02; A61K 31/22
[52] U.S. Cl. .................... 514/550; 514/558; 514/560; 260/399; 260/400; 260/413
[58] Field of Search ............. 514/546, 550, 557; 260/399, 400, 413

[56] References Cited

FOREIGN PATENT DOCUMENTS 2208533 9/1973 Fed. Rep. of Germany.

OTHER PUBLICATIONS van Leusen et al., Chemical Abstracts, vol. 62 (1965) No. 13075f.
Chauveau et al., Chemical Abstracts, vol. 60 (1964) No. 11886a.
Burness, Chemical Abstracts, vol. 54, No. 256d.
Hato et al., Bull. Chem. Soc. Japan, vol. 49(5) pp. 1257–1259 (1976).
Mayer et al., Chim. Ther., vol. 3 (No. 5) (1968).
Aveta et al., Gazz. Chim. Italy, vol. 116, No. 11 (1986).
Gershon et al., J. Parhm. Science, vol. 68, No. 1, 1979.
Chemical Abstracts, vol. 64, No. 15735c.
Orsymonde S. A., Chemical Abstracts, vol. 66 (1967) No. 65110t.
Bairamova et al., Prisadki Smaz. Maslarn, vol. 7, 1981 (pp. 19–23).

*Primary Examiner*—Jose G. Dees
*Assistant Examiner*—Deborah D. Carr
*Attorney, Agent, or Firm*—Wenderoth, Lind & Ponack

[57] ABSTRACT

A method is provided for the treatment of hypolipaemic conditions and for reducing the concentration of cholesterol and triglycerides in the blood of mammals. The method comprises administering to a mammal an effective amount of non-β-oxidizable fatty acid analogue of the formula Alkyl-X-$CH_2$COOR where the alkyl group is a saturated or unsaturated hydrocarbon chain of 8 to 22 carbon atoms, where X represents an oxygen atom, a sulfur atom, a sulfoxide (SO) or sulfone ($SO_2$) group and where R is a hydrogen atom or an alkyl group of 1 to 4 carbon atoms. Pharmaceutical compositions are also provided.

5 Claims, 2 Drawing Sheets

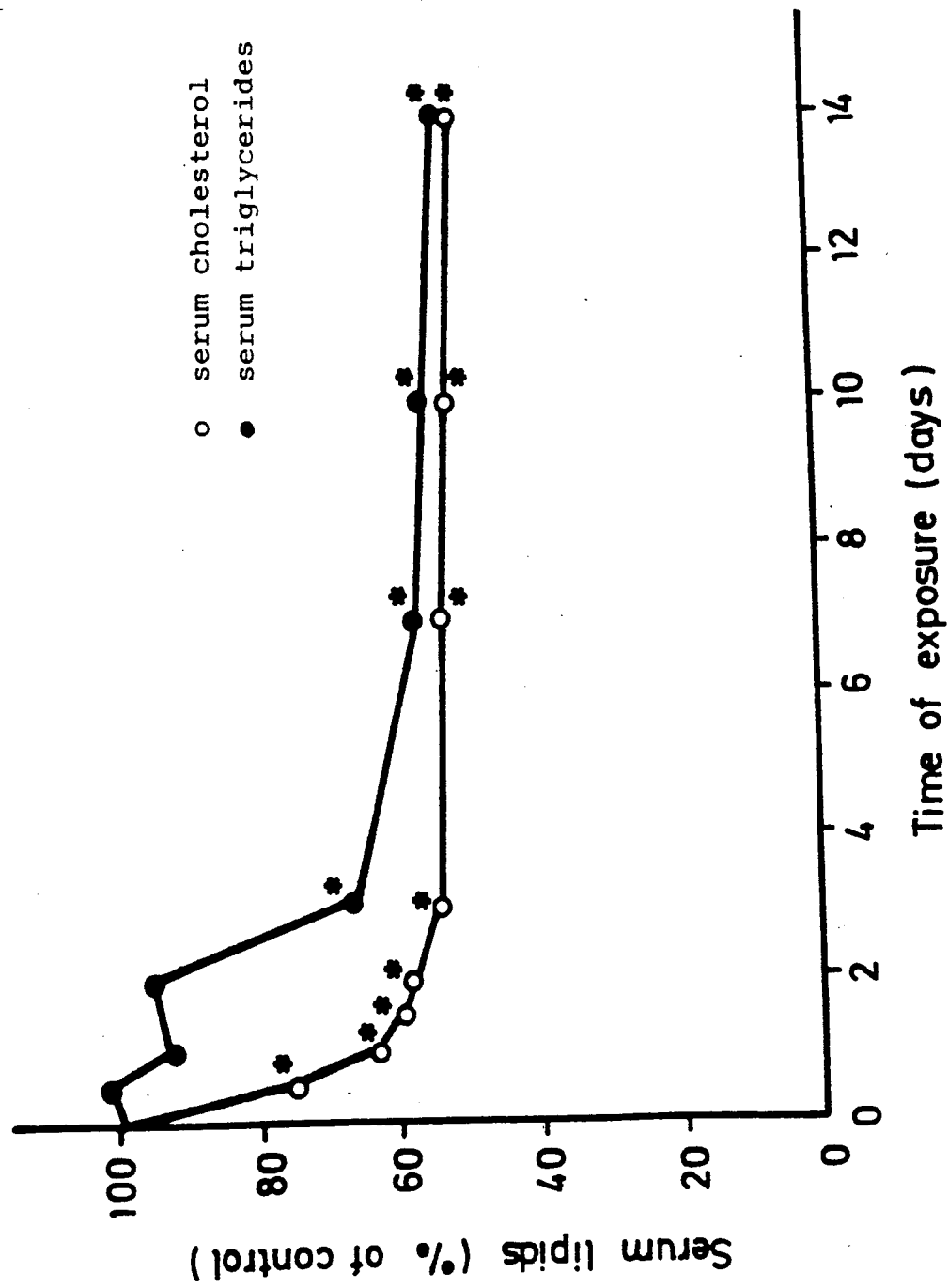

NON-β-OXIDIZABLE FATTY ACID ANALOGUES WITH THE EFFECT TO REDUCE THE CONCENTRATION OF CHOLESTEROL AND TRIGLYCERIDES IN BLOOD OF MAMMALS

This invention relates to novel non-β-oxidizable fatty acid analogues having the effect of reducing the concentration of cholesterol and triglycerides in the blood of mammals.

An excess of lipids in blood has been shown to accelerate the development of arteriosclerosis and is a risk factor for myocardial infarction. Accordingly, a reduction of the concentration of lipids in the blood by diet or by drugs is used as a preventive measure in people at risk due to high blood levels of cholesterol and triglycerides.

It is well known that some natural long-chain fatty acids, particularly polyunsaturated fatty acids of marine origin, are effective in lowering plasma triglyceride and possibly cholesterol levels in man. Experimental studies in animals have shown that these fatty acids enhance fatty acid oxidation, partly by increased peroxisomal activity, depress synthesis of fatty acids, and decrease synthesis of apolipoprotein B and product of VLDL.

Similar effects are obtained with a series of peroxisome proliferating, hypolipaemic drugs like clofibrate, bezafibrate, tiadenol and others which have more complicated chemical structures. These compounds, however, are generally more toxic and have several undesirable side effects.

Considering that the polyunsaturated long chain fatty acids are metabolized relatively slowly, we postulated that simply non-β-oxidizable fatty acids analogues might have similar effects. In feeding experiments with such new fatty acid analogues the results show that they lower the blood concentration of cholesterol and triglyceride, without any overt toxic effect.

They induce some increased peroxisomal β-oxidation activity. These fatty acid analogues are to our best knowledge the simplest lipid-lowering compounds found so far.

SUMMARY OF THE INVENTION

An objective of the present invention is to provide novel fatty acid analogues having the ability to lower the concentration of cholesterol and triglyceride in the blood and with improved effect relative to the conventional drugs clofibrate, bezafibrate and tiadenol and without the undesirable side effects of these drugs.

DETAILED DESCRIPTION OF THE INVENTION

Figure 1:
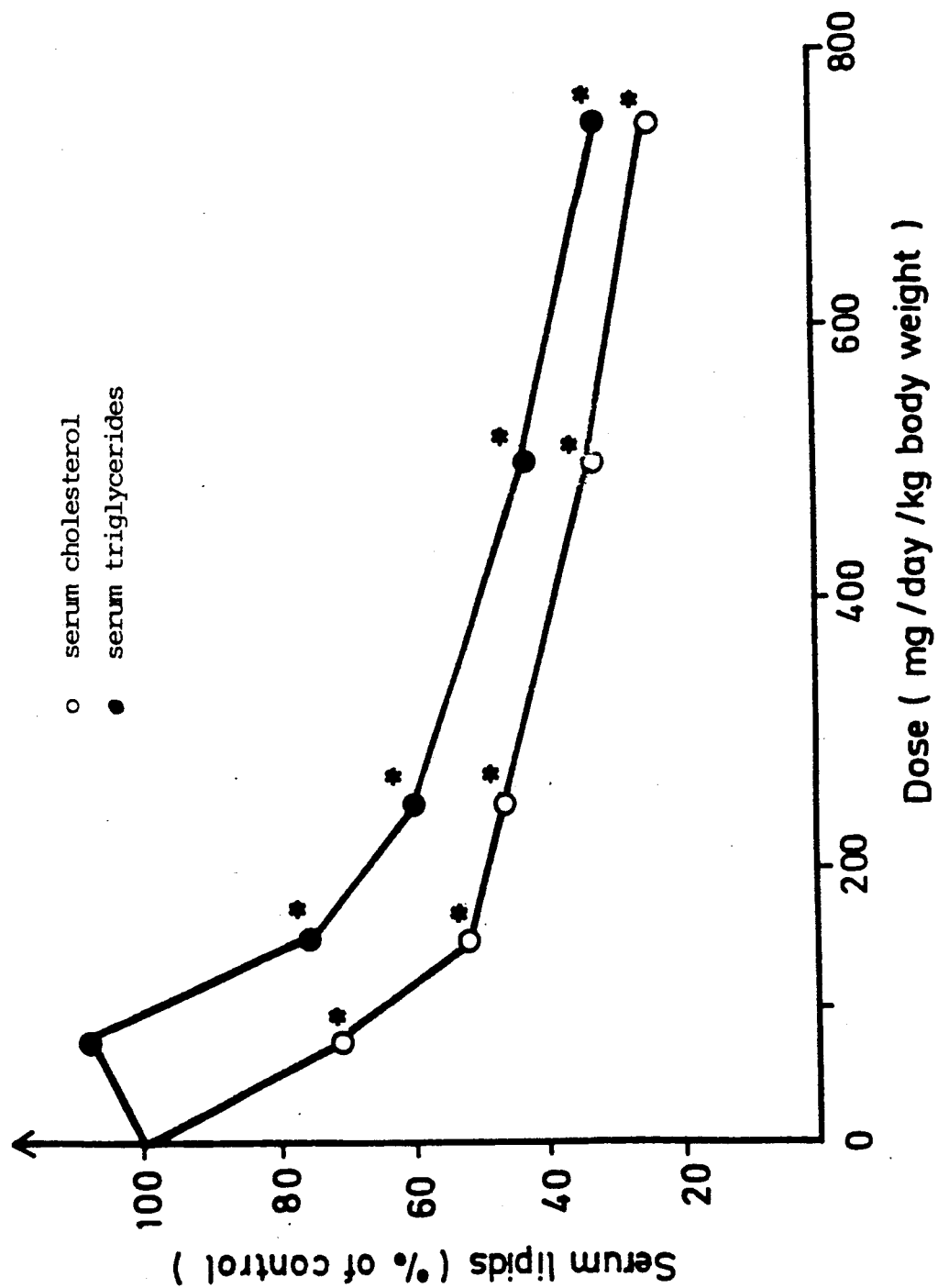

The compounds of the present invention are fatty acid derivatives represented by the general formula Alkyl—X—CH$_2$COOR where the alkyl group is a saturated or unsaturated hydrocarbon chain of at least 8 carbons, e.g., of from 8 to 22 carbon atoms, where X represents an oxygen atom, a sulfur atom, a sulfoxide (SO) or a sulfone (SO$_2$) group, and where R is a hydrogen atom, or a short alkyl group, e.g., of 1 to 4 carbon atoms, such as ethyl.

Several compounds under this general formula have been synthetized and tested by the inventors. The compounds can be prepared for example by the following methods.

The compounds according to the present application where X is an oxygen or a sulphur atom may be prepared according to the following general procedure:

The thio compounds according to the present application may also be prepared as indicated below:

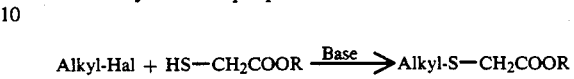

The sulfoxide or sulfone groups may be prepared by oxidation of a thio compound with an oxidizing agent such as hydrogen peroxide:

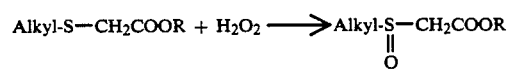

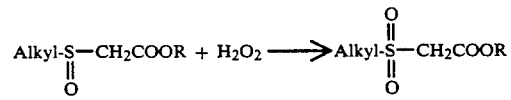

Further, the oxygen ethers according to present application may be prepared according to the procedure shown below:

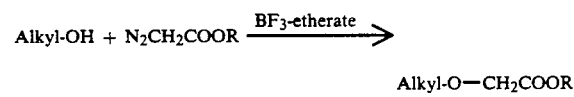

The conversion of the esters (R being a short alkyl group) in the acids may be accomplished using the following well-known procedure:

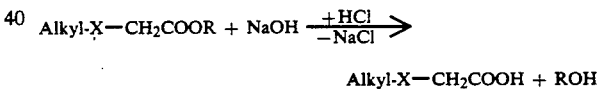

The following examples illustrate the preparation of a series of especially preferred compounds:

EXAMPLES

1. S-Tetradecylthioacetic acid
CH$_3$—(CH$_2$)$_{13}$—S—CH$_2$COOH

KOH, 20 g (0.3 equivalents), mercaptoacetic acid (12 ml, 0.14 equivalents), and tetradecylbromide (25 ml, 0.09 equivalents) were added in that order to 200 ml methanol and stirred overnight under nitrogen. A white precipitate of potassium bromide was formed. To the reaction mixture was added concentrated HCl (30 ml) and water (400 ml). The precipitate sedimented by centrifugation was washed twice with water (750 ml) and dissolved in 500 ml 90% hot methanol. After cooling and crystallization at room temperature the precipitate was recrystallized from 600 ml hot 75% ethanol The tetradecylthioacetic acid crystallized as white flakes and was isolated by filtration.

Yield: 23 g = 75% based on the amount of tetradecylbromide used.

Thin layer chromatography on silica plates with hexane-ethylether formic acid (60:40:1) gave only one spot with iodine vapour, R$_f$=approximately 0.6.

2. Tetradecylthioacetic acid sulfoxide

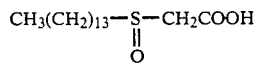

Tetradecylthioacetic acid (5.75 g, 20 mmol) was dissolved in 60 ml acetone Hydrogen peroxide (2.25 ml, 30%) was added and the mixture left overnight at room temperature. Additional hydrogen peroxide (0.5 ml, 30%) was added and the mixture left for another 24 h. The reaction mixture was evaporated to dryness in vacuo at room temperature. Thin layer chromatography showed some remaining unchanged tetradecylthioacetic acid. Crystallization twice from hot acetone removed the tetradecylthioacetic acid.

Yield: 4.5 g=75%.

3. Tetradecylthioacetic acid sulfone

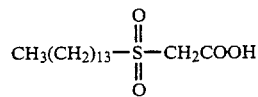

5.75 tetradecylthioacetic acid was dissolved in 60 ml acetone and hydrogen peroxide (30%, 5 ml) was added. The mixture was left overnight at approximately 40°. To the reaction mixture was added additional 40 ml acetone and 10 ml H$_2$O. Upon cooling the sulfone precipitated. Thin layer chromatography on silica plates showed only one spot in iodine vapour (hexane-ethylether-formic acid) (60:40:1).

| | |
|---|---|
| R$_f$ values: tetradecylthioacetic acid | 0.6 |
| R$_f$ values: tetradecylthioacetic sulfoxide | 0.1 |
| R$_f$ values: tetradecylthioacetic sulfone | 0.2 |

4. Ethyl tetradecyloxy acetate
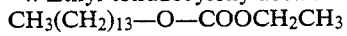

Tetradecanol (23.6 g, 0.11 Mol) and ethyl diazoacetate (14.4 g, 0.13 Mol) was dissolved in 140 ml dichloromethane and the mixture was cooled to 0° C. Boron trifluoride ethyl etherate (3 ml) dissolved in 10 ml dichloromethane was added to the stirred solution during 10 minutes. Subsequently the solution was stirred at room temperature for 45 minutes and thereafter washed with water and dried (MgSO$_4$) Dichloromethane was vaporized on a rotavapor and the product was purified by distillation at reduced pressure.

Yield: 20.5 g (62%), b.p. 120–125° C./0.01 mmHg.

5. Tetradecyloxy acetic acid CH$_3$(CH$_2$)$_{13}$OCH$_2$COOH

Ethyl tetradecyloxyacetate (18.0 g, 0.06 mol) was dissolved in methanol (80 ml) and a solution of NaOH (8.0 g, 0.20 Mol) dissolved in water (50 ml) was added and the mixture was refluxed for 5 hours. After cooling the reaction mixture was washed with hexane, acidified with hydrochloric acid and extracted with ether. The ether extracts were washed with water and dried over MgSO$_4$. The residue after vaporization of the solvent was recrystallized from ether/hexane.

Yield: 14.9 g (91%) m.p. 58°–59° C.

Experiments

Male Wistar rats, weighing 180–200 g at the start of the experiment, were housed individually in metal wire cages in a room maintained at 12 h light-dark cycles and a constant temperature of 20±3° C. The animals were acclimatized for at least 5 days under these conditions before the start of the experiments.

Compound I (tetradecylthioacetic acid), and other fatty acid derivatives according to the invention, were suspended in 0.5 % (w/v) carboxymethyl cellulose (CMC) and the suspension was micronized by ultrasonication. The drugs were administered by gastric intubation (gavage) once daily for 5 days. Results obtained with compound I are reported in FIG. 1 and FIG. 2, wherein:

FIG. 1 shows the effect of the dose of compound I on serum cholesterol (o) and triglycerides (○ ). *p 0.05 compared to the control group; and FIG. 2 shows the effect of compound I at a dose of 150 mg/day/kg body weight on serum cholesterol (o) and triglycerides (○ ). *p 0.05 compared to the control group.

The hypolipidemic effect as a function of dose administered is shown in FIG. 1. A time-course study (from 12 h up to 14 days) of the hypolipidemic effects were examined with a dose of 150 mg/day/kg body weight (see FIG. 2). Four animals were used for each treatment and a 0.5% CMC solution only was administered to rats as control. After administration of the test compound, rats were fasted for 12 hours and anesthetized with haloethan. Blood samples were collected by cardiac puncture, and lipid concentrations in serum were determined using an autoanalyzer. Liver was removed at the same time, and it was homogenized in ice-cold sucrose medium (0.25 M sucrose, 10 mM Hepes buffer, pH 7.4 and mM EDTA). A 10% liver homogenate was made and peroxisomal β-oxidation was measured. The effects of the compounds were compared with that of clofibrate, tiadenol and niadenate. These drugs were suspended and administered at a dose of 150 mg/day/kg body weight to rats in a similar way as compound I. The dosing lasted for 10 days and the data obtained are shown in Table 1.

TABLE 1

Effect of compound I and different hypolipidemic drugs on the liver weight and peroxisomal beta-oxidation in rat liver homogenates

| Compounds | Liver weight/ body weight | Peroxisomal β-oxidation (nmol/min/g liver) |
|---|---|---|
| Control | 4.1 ± 0.1 | 340 ± 30 |
| Compound I | 4.3 ± 0.2 | 460 ± 40** |
| Clofibrate | 5.7 ± 0.2* | 1120 ± 60* |
| Tiadenol | 6.9 ± 0.3* | 1450 ± 80* |
| Niadenate | 7.3 ± 0.2* | 1480 ± 90* |

Values represent means ± S.D. of four rats. Statistically significant differences from the controls:
*p < 0.01, **p < 0.05.

Values represent means ±S.D. of four rats. Statistically significant differences from the controls:
*p<0.01, **p<0.05.

Table 1 clearly shows the superior property of the compound I regarding adverse side effects at doses that give comparable lipid lowering.

Further, FIGS. 1 and 2 show that compound I can achieve a significant reduction in serum lipids.

The compounds according to the invention thus exhibit a good hypolipidemic effect in blood of mammals such as rats and possess low toxicity measured as increase in liver weight and increased peroxisomal β-oxidation. The compounds exhibit a good hypolipidemic effect in rats, but lower toxicity compared to the comparative drugs (clofibrate, tiadenol and niadenate). Therefore they may be useful as medicinal compounds. For such purposes, the compounds of the present invention can be administered orally or parenterally in a conventional dosage form such as tablets, capsules, powders, emulsions and solutions prepared according to conventional pharmaceutical practices.

The compounds according to present application may be administered to patients suffering from any type of dyslipidaemia except type I.

The dosage range for the compounds according to the present application is contemplated to be from 100–1000 mg/day for the average adult patient.

The actual dose necessary will depend on the patient's condition and will have to be determined by the attending physical from case to case.

The compounds according to the present application may be administered in any suitable pharmaceutical composition, alone or in admixture with the commonly used pharmaceutical carrier materials. For oral pharmaceutical compositions such carrier materials may be for example water, gelatin, gums, lactose, starches, magnesium stearate, talc, oils, polyalkylene glycol, petroleum jelly and the like. Such pharmaceutical preparations may be in unit dosage form and may additionally contain other therapeutically valuable substances or conventional pharmaceutical adjuvants such as preservatives, stabilizing agents, wetting agents, emulsifying agents, buffers and the like. The pharmaceutical preparations may be in the conventional solid dosage forms such as tablets, capsules, dragees, and the like, in conventional liquid forms such as solutions, suspensions, emulsions and the like and other conventional dosage forms such as dry ampules, suppositories and the like.

For parenteral administration the compounds according to the present application may be administered as solutions, suspensions or emulsions using conventional pharmaceutical carrier materials such as for example water for injection, oils, polyalkylene glycols and the like. These pharmaceutical preparations may further include conventional pharmaceutical adjuvants such as preservatives, stabilizing agents, wetting agents, emulsifying agents, salts for the adjustment of the osmotic pressure, buffers and the like. The preparations may also contain other therapeutically active materials.

What is claimed is:

1. A method for the treatment of hypolipaemic conditions and for reducing the concentration of cholesterol and triglycerides in the blood of mammals which comprises administering to a mammal an effective amount of non-$\beta$-oxidizable fatty acid analogue of the formula

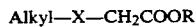

where the alkyl group is a saturated or unsaturated hydrocarbon chain of 8 to 22 carbon atoms, where X represents an oxygen atom, a sulfur atom, a sulfoxide (SO) or sulfone ($SO_2$) group and where R is a hydrogen atom or an alkyl group of 1 to 4 carbon atoms.

2. A method according to claim 1 where the analogue is S-tetradecylthioacetic acid.

3. A method according to claim 1 where the analogue is tetradecylthioacetic acid sulfoxide.

4. A method according to claim 1 where the analogue is tetradecylthioacetic acid sulfone.

5. A method according to claim 1 wherein R is ethyl.

* * * * *

UNITED STATES PATENT AND TRADEMARK OFFICE
CERTIFICATE OF CORRECTION

PATENT NO. : 5,093,365

DATED : March 3, 1992

INVENTOR(S) : ROLF K. BERGE and JON BREMER

It is certified that error appears in the above-identified patent and that said Letters Patent is hereby corrected as shown below:

On the cover page of the patent, in the ABSTRACT, line 1, change "hypolipaemic" to read —hyperlipidemic—.

Column 1, line 5, delete "product" and insert therefor —production—.

Column 5, line 18, delete "physical" and insert therefor —physician—.

Column 6, line 15, delete "hypolipaemic" and insert —hyperlipidemic—.

Signed and Sealed this

Tenth Day of August, 1993

Attest:

MICHAEL K. KIRK

Attesting Officer

Acting Commissioner of Patents and Trademarks